United States Patent
Maeda

(10) Patent No.: US 10,624,527 B2
(45) Date of Patent: Apr. 21, 2020

(54) MANUFACTURING METHOD OF OPTICAL UNIT FOR ENDOSCOPE, OPTICAL UNIT FOR ENDOSCOPE, AND ENDOSCOPE

(71) Applicant: OLYMPUS CORPORATION, Tokyo (JP)

(72) Inventor: Kazuya Maeda, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/204,575

(22) Filed: Nov. 29, 2018

(65) Prior Publication Data
US 2019/0090720 A1 Mar. 28, 2019

Related U.S. Application Data

(63) Continuation of application No. PCT/JP2016/066737, filed on Jun. 6, 2016.

(51) Int. Cl.
*A61B 1/00* (2006.01)
*G02B 23/24* (2006.01)
(Continued)

(52) U.S. Cl.
CPC ........ *A61B 1/0011* (2013.01); *A61B 1/00096* (2013.01); *A61B 1/00186* (2013.01);
(Continued)

(58) Field of Classification Search
CPC .............. A61B 1/0011; A61B 1/00186; A61B 1/00096; G02B 7/02; G02B 23/2423;
(Continued)

(56) References Cited

U.S. PATENT DOCUMENTS 9,625,684 B2 * 4/2017 Norton ............... G02B 13/0085
2002/0186478 A1 * 12/2002 Watanabe ................ G02B 7/02
359/819

(Continued)

FOREIGN PATENT DOCUMENTS

JP  2010-102313 A  5/2010
JP  2011-095337 A  5/2011
(Continued)

OTHER PUBLICATIONS

International Search Report dated Aug. 16, 2016 issued in PCT/JP2016/066737.

*Primary Examiner* — Abdelaaziz Tissire
(74) *Attorney, Agent, or Firm* — Scully, Scott, Murphy & Presser, P.C.

(57) ABSTRACT

A manufacturing method of an optical unit for endoscope includes: a process of fabricating a plurality of element wafers each including an optical element having an optical path portion and a spacer portion; a first adhesion process of fabricating a laminated wafer by adhering the element wafers with a first adhesive portion composed of a solid first adhesive disposed in a gap between the spacer portions; a second adhesion process of fabricating a bonded wafer by injecting a liquid second adhesive in the gap between the spacer portions; a curing process of performing curing treatment on the second adhesive; and a process of cutting the bonded wafer.

14 Claims, 11 Drawing Sheets

(51) Int. Cl.
*H04N 5/225* (2006.01)
*G02B 7/02* (2006.01)
(52) U.S. Cl.
CPC ............ *G02B 7/02* (2013.01); *G02B 23/2423* (2013.01); *H04N 5/2253* (2013.01); *H04N 5/2254* (2013.01); *H04N 5/2257* (2013.01)
(58) Field of Classification Search
CPC ...... G02B 23/243; G02B 7/021; G02B 7/003; G02B 7/023; G02B 7/025; H04N 17/002; H04N 5/2257; H04N 5/2254; H04N 5/2253
See application file for complete search history.

(56) References Cited

U.S. PATENT DOCUMENTS

| | | | | |
|---|---|---|---|---|
| 2010/0073531 | A1* | 3/2010 | Yano | B26D 3/08 348/294 |
| 2010/0265597 | A1* | 10/2010 | Shyu | C03B 11/08 359/797 |
| 2011/0149143 | A1* | 6/2011 | Tsujino | G02B 3/0031 348/374 |
| 2012/0154923 | A1* | 6/2012 | Lee | G02B 13/001 359/642 |
| 2013/0242182 | A1* | 9/2013 | Rudmann | G02B 7/021 348/374 |
| 2014/0058201 | A1* | 2/2014 | Mizuyoshi | G02B 23/2423 600/129 |
| 2014/0334021 | A1* | 11/2014 | Norton | G02B 13/0085 359/793 |
| 2017/0038562 | A1* | 2/2017 | Georgiev | G02B 7/003 |

FOREIGN PATENT DOCUMENTS

| | | | |
|---|---|---|---|
| JP | 2011-097144 | A | 5/2011 |
| JP | 2011-118166 | A | 6/2011 |
| JP | 2011-128355 | A | 6/2011 |
| JP | 2012-018993 | A | 1/2012 |
| JP | 2012-226202 | A | 11/2012 |
| JP | 2012226202 | A * | 11/2012 |

* cited by examiner

MANUFACTURING METHOD OF OPTICAL UNIT FOR ENDOSCOPE, OPTICAL UNIT FOR ENDOSCOPE, AND ENDOSCOPE

CROSS REFERENCE TO RELATED APPLICATION

This application is a continuation application of PCT/JP2016/066737 filed on Jun. 6, 2016, the entire contents of which are incorporated herein by this reference.

BACKGROUND OF INVENTION

1. Field of the Invention

The present invention relates to a manufacturing method of an optical unit for endoscope configured by laminating a plurality of optical elements, an optical unit for endoscope configured by laminating a plurality of optical elements, and an endoscope including an optical unit for endoscope configured by laminating a plurality of optical elements.

2. Description of the Related Art

In an optical unit for endoscope to be disposed at a distal end portion of an endoscope, size reduction, in particular, reduction in the diameter size is significant for achieving low invasiveness.

Japanese Patent Application Laid-Open Publication No. 2012-18993 discloses a manufacturing method of an optical unit constituted of a wafer-level laminated body, as a method of efficiently manufacturing an optical unit. The wafer-level optical unit is fabricated by cutting and segmenting a bonded wafer formed by laminating a plurality of element wafers each including a plurality of optical elements and adhering the plurality of element wafers to each other.

SUMMARY OF THE INVENTION

A manufacturing method of an optical unit for endoscope according to an embodiment of the present invention includes: a process of fabricating a plurality of element wafers each including an optical element, the optical element including an optical path portion and a spacer portion surrounding the optical path portion and forming an optical path space; a first adhesion process of arranging the plurality of element wafers such that optical axes of the optical elements coincide with each other, adhering the element wafers opposed to each other with a first adhesive portion composed of a solid first adhesive disposed between the spacer portions of the element wafers opposed to each other, to thereby fabricate a laminated wafer; a second adhesion process of fabricating a bonded wafer by injecting a liquid second adhesive in a gap between the spacer portions; a curing process of performing curing treatment on the liquid second adhesive to form a second adhesive portion; and a process of cutting the bonded wafer.

An optical unit for endoscope according to an embodiment includes: a plurality of optical elements each including an optical path portion and a spacer portion surrounding the optical path portion and forming an optical path space, the plurality of optical elements being laminated, the optical elements opposed to each other being adhered to each other with an adhesive portion disposed between the spacer portions, wherein the adhesive portion includes a first adhesive portion composed of a first adhesive and a second adhesive portion composed of a second adhesive, and the optical path space is surrounded by the second adhesive portion with no gap left.

An endoscope according to an embodiment includes an optical unit for endoscope, and the optical unit for endoscope includes a plurality of optical elements each including an optical path portion and a spacer portion surrounding the optical path portion and forming an optical path space, the plurality of optical elements being laminated, the optical elements opposed to each other being adhered to each other with an adhesive portion disposed between the spacer portions, wherein the adhesive portion includes a first adhesive portion composed of a first adhesive and a second adhesive portion composed of a second adhesive, and the optical path space is surrounded by the second adhesive portion with no gap left.

DETAILED DESCRIPTION OF THE PREFERRED EMBODIMENT(S)

First Embodiment

Figure 1:
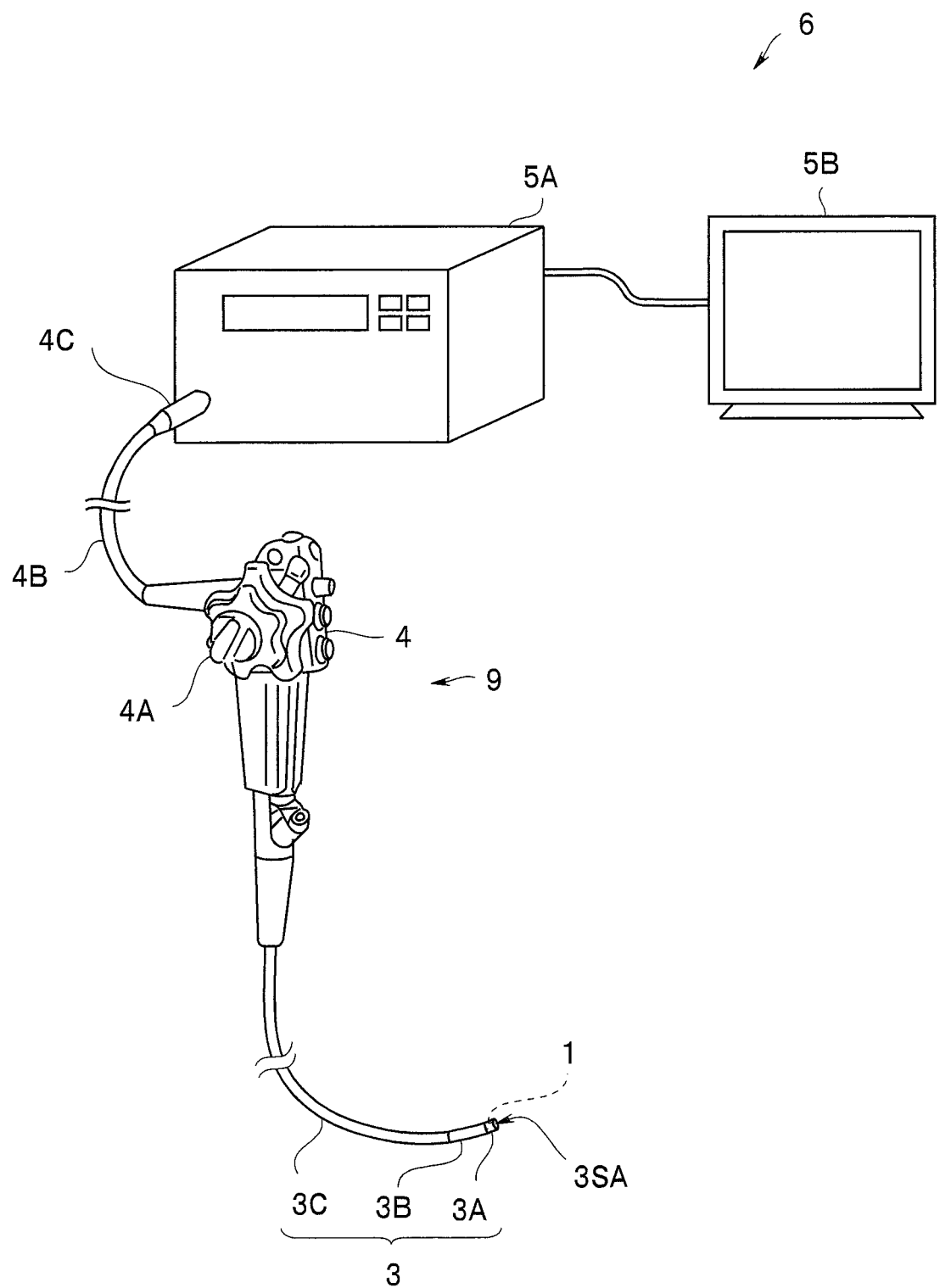
FIG. 1 is a perspective view of an endoscope according to an embodiment.

As shown in FIG. 1, an optical unit for endoscope 1 (hereinafter, also referred to as "optical unit 1") according to the present embodiment is disposed at a distal end portion 3A of an insertion portion 3 of an endoscope 9.

Note that each of the drawings based on each of the embodiments is a pattern diagram in the description below, and care should be taken to the fact that the relationship between the thicknesses and widths of the respective parts, a ratio of the thicknesses, relative angles, and the like of the respective parts are different from the actual ones, and there is a case where the respective drawings include the parts in which the relationships and ratios among the dimensions are different from those in other drawings. In addition, there is a case where illustration of some constituent elements is omitted.

An endoscope 9 includes an insertion portion 3, a grasping portion 4 disposed on a proximal end portion side of the insertion portion 3, a universal cord 4B extended from the grasping portion 4, and a connector 4C disposed on a proximal end portion side of the universal cord 4B. The insertion portion 3 includes a distal end portion 3A at which the optical unit 1 is disposed, a bending portion 3B extended from the proximal end side of the distal end portion 3A and configured to be bendable and configured to change a direction of the distal end portion 3A, and a flexible portion 3C extended from the proximal end side of the bending portion 3B. The optical unit 1 includes a light incident surface 10SAA (see FIG. 2) exposed on a distal end surface 3SA of the distal end portion 3A. The grasping portion 4 is provided with an angle knob 4A configured to rotate. The angle knob 4A is an operation portion configured to be operated by an operator to operate the bending portion 3B.

The universal cord 4B is connected to the processor 5A through a connector 4C. The processor 5A is configured to control an entire endoscope system 6, perform signal processing on an image pickup signal outputted from the optical unit 1, and output the image pickup signal subjected to the signal processing as an image signal. A monitor 5B displays the image signal outputted from the processor 5A as an endoscopic image. Note that the endoscope 9 is a flexible endoscope. However, the endoscope 9 may be a rigid endoscope as long as the endoscope includes a bending portion. That is, the flexible portion and the like are not essential constituent elements of the endoscope according to the embodiment. In addition, the endoscope according to the embodiment may be a capsule endoscope including the optical unit 1.

<Configuration of Optical Unit>

Figure 2:
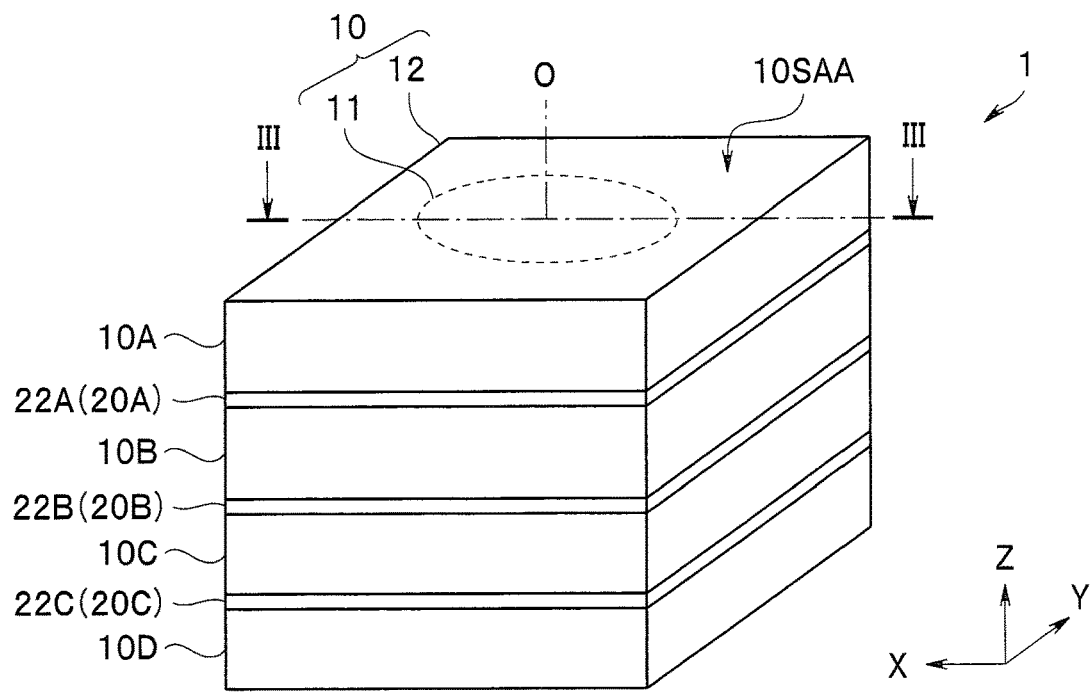
FIG. 2 is a perspective view of an optical unit according to a first embodiment.
Figure 3:
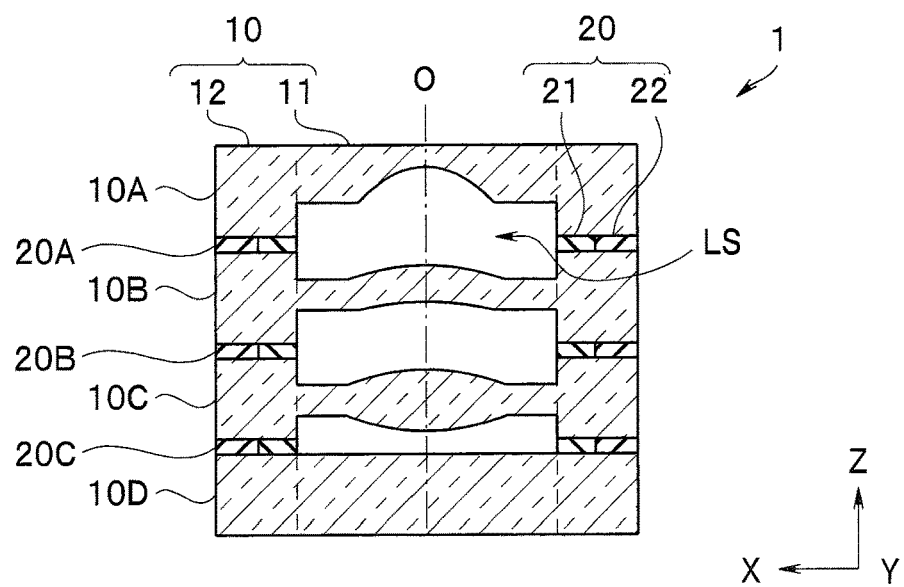
FIG. 3 is a cross-sectional view taken along the line III-III in FIG. 2 of the optical unit according to the first embodiment.
Figure 4:
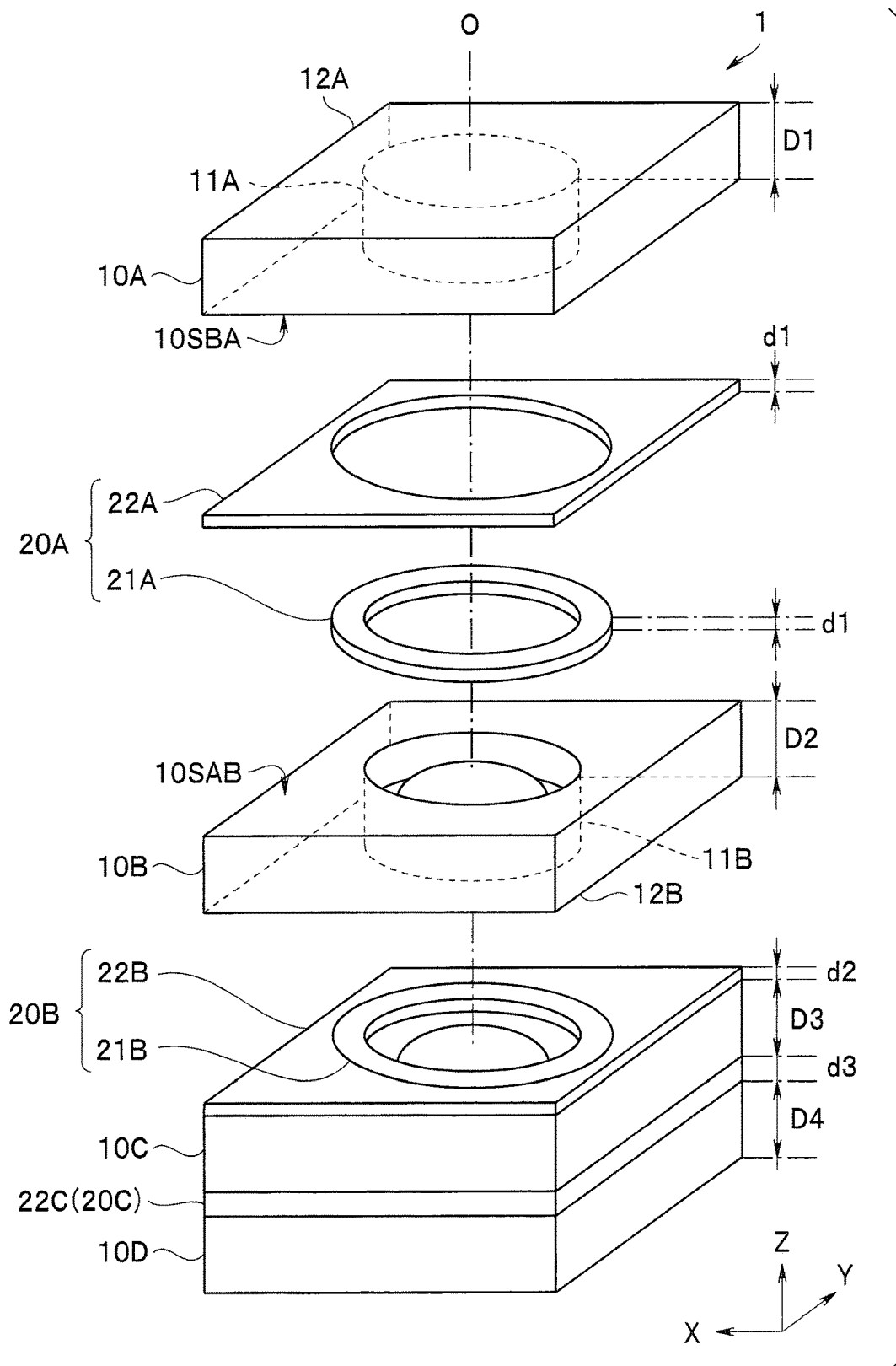
FIG. 4 is an exploded view of the optical unit according to the first embodiment.

As shown in FIGS. 2 to 4, the optical unit for endoscope 1 is a laminated body formed by laminating a plurality of optical elements 10A to 10D. The plurality of optical elements 10A to 10D are adhered to each other with adhesive portions 20A to 20C disposed between the respective optical elements.

Note that, hereinafter, when referring to a plurality of respective constituent elements, one alphabetic character at the end of the respective reference signs will be omitted. For example, the respective optical elements 10A to 10D will be referred to as the optical element 10.

Figure 11:
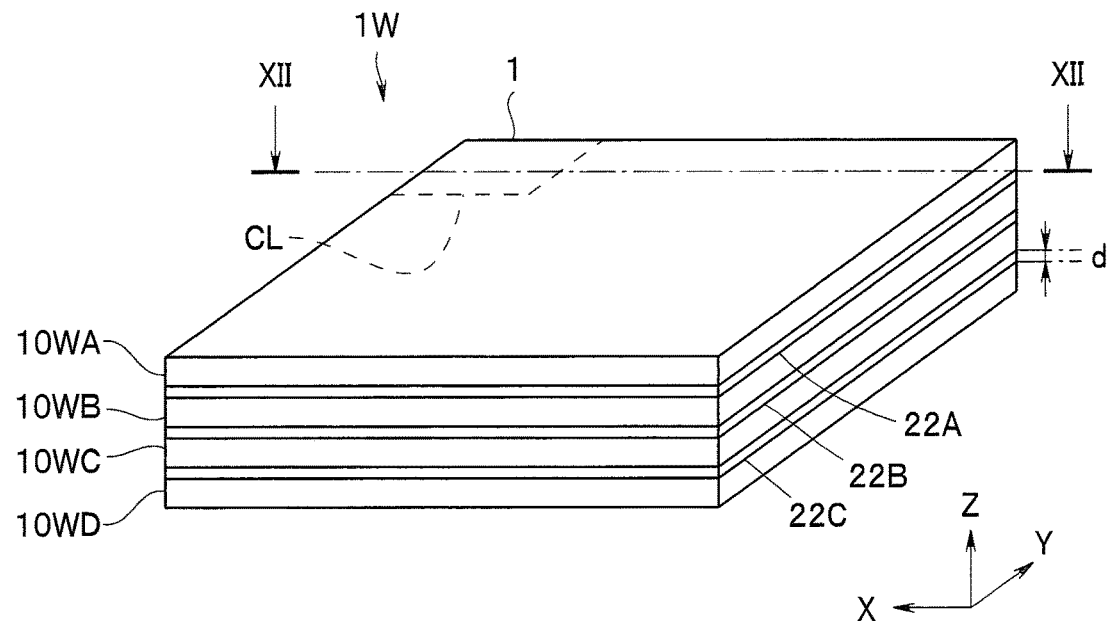
FIG. 11 is a perspective view of a bonded wafer of the optical unit according to the first embodiment.
Figure 12:
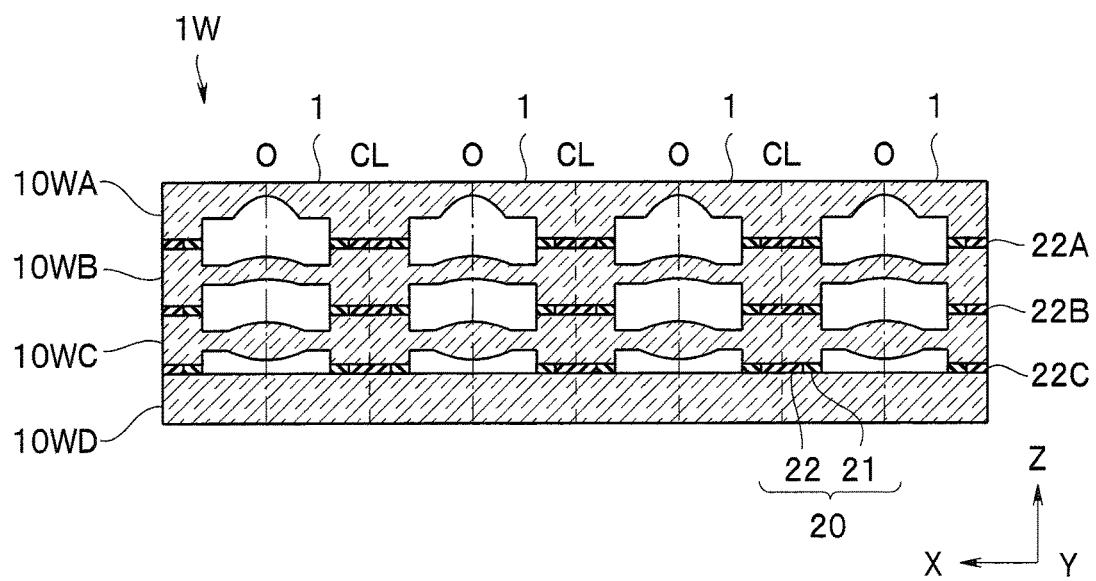
FIG. 12 is a cross-sectional view taken along the line XII-XII in FIG. 11 of the bonded wafer of the optical unit according to the first embodiment.

As described later, the optical unit 1 is a wafer-level optical unit fabricated by cutting a bonded wafer 1W (see FIG. 11). Therefore, the optical unit 1 according to the present embodiment has a rectangular parallelepiped shape, and the optical elements 10A to 10D and the adhesive portions 20A to 20C have a rectangular shape in the cross section taken along the direction orthogonal to the optical axis and have the same outer dimension. The optical elements 10A to 10D are laminated such that the optical axes O of the respective optical elements coincide with each other.

The optical element 10 includes an optical path portion 11 that forms an optical path and a ring-shaped spacer portion 12 configured to surround the optical path portion 11 and form an optical path space S. For example, an optical path portion 11A of the optical element 10A has a circular shape in a plan view, and one surface of the optical path portion 11A is a concave lens. The spacer portion 12A has a square outer shape and a circular inner shape in a plan view, and includes a flat surface protruded with respect to the optical path portion 11A. For example, the space, which is surrounded by the two spacer portions 12 of the optical elements 10A and 10B opposed to each other, is an optical path space LS that forms the optical path.

The optical path portion of the optical elements 10B has one surface which is a convex shape, and the other surface which is a concave shape. Both surfaces of the optical path portion of the optical element 10C are formed in a convex shape. The optical element 10D is an infrared cut filter made of a parallel flat plate.

The adhesive portion 20 disposed between the spacer portions 12 of the optical elements 10 opposed to each other includes a ring-shaped first adhesive portion 21 disposed in a region close to the optical path space LS and a second adhesive portion 22 disposed around the first adhesive portion 21. That is, the optical path space LS is surrounded by the first adhesive portion 21 with no gap left, and the first adhesive portion 21 is surrounded by the second adhesive portion 22 with no gap left. Therefore, the optical path space LS is surrounded also by the ring-shaped second adhesive portion 22 with no gap left.

As described later, the first adhesive portion 21 is composed of a solid first adhesive, and patterned in a predetermined shape, that is, a ring shape. On the other hand, the second adhesive portion 22 is disposed by performing curing treatment on an uncured liquid second adhesive injected into a gap having a thickness (distance) d between the spacer portions 12 of the optical elements opposed to each other, which is created by the thickness of the first adhesive portion 21 disposed between the spacer portions 12.

For example, a second principal surface 10SBA of the optical element 10A and the first principal surface 10SAB of the optical element 10B are bonded to each other with the ring-shaped first adhesive portion 21A and with the second adhesive portion 22A having a ring shape to surround the first adhesive portion 21A with no gap left and having side surfaces exposed on the side surfaces of the optical unit 1. The first adhesive portion 21A and the second adhesive portion 22A have the same thickness d1.

Note that the thicknesses D1 to D4 of the optical elements 10A to 10D and the thicknesses d1 to d3 of the adhesive portions 20A to 20C are set according to specifications.

Note that the optical unit 1 also includes other optical elements such as a flare diaphragm and a brightness diaphragm, though not shown. In addition, any one of the optical elements may be a spacer element including, at the center thereof, a through hole which serves as an optical path. That is, the configuration of the optical unit according to the embodiment is not limited to the configuration of the optical unit 1. The configuration such as the numbers of the optical elements, spacers, and the diaphragms are set according to the specifications of the optical unit.

As described above, the optical unit for endoscope 1 is fabricated by laminating the plurality of optical elements 10A to 10D each having the optical path portion 11 and the spacer portion 12 surrounding the optical path portion 11 and adhering a pair of opposed optical elements to each other with the adhesive portion 20 disposed between the spacer portions of the opposed optical elements. The adhesive portion 20 includes the ring-shaped first adhesive portion composed of the first adhesive and surrounding the optical path space LS with no gap left, and the second adhesive portion 22 composed of the second adhesive. That is, also the ring-shaped second adhesive portion 22 surrounds the optical path space LS with no gap left. The second adhesive portion 22 surrounds the periphery of the first adhesive portion 21A with no gap left, and includes the side surfaces exposed on the outer surfaces of the optical unit 1, and has the thickness same as that of the first adhesive portion 21A.

If a liquid material is used as the adhesive for adhering the element wafers to each other, the adhesive protrudes to the optical path, which may have a bad influence on the optical property of the optical unit. Therefore, manufacturing of the optical unit was not easy. On the other hand, if a solid material is used as the adhesive, patterning has to be performed for removing the adhesive in the optical path region to form an opening. If a photosensitive adhesive is used, high-precision patterning can be performed by photolithography method. However, the adhesive strength is not sufficient, which may result in degradation in reliability of the segmented optical unit.

In order to achieve the low invasiveness of the endoscope 9, the optical unit 1 is configured such that the cross section of the optical element 10 is extremely thin, for example, 1 mm square or smaller. Therefore, the outer diameter of the cross section of the optical path space is 0.75 mm or smaller, for example. Accordingly, it is not easy to adhere the plurality of optical elements 10 (element wafers 10W) to each other. However, in the optical unit 1, there is no possibility that the adhesive protrudes to the optical path space, which leads to easy manufacturing. In addition, the optical elements 10 are strongly adhered to each other with the adhesive portions 20, which results in high reliability of the optical unit.

As a result, the endoscope 9 including the optical unit 1 has a thin diameter, and enables easy manufacturing and high reliability.

<Manufacturing Method of Optical Unit for Endoscope>

Figure 5:
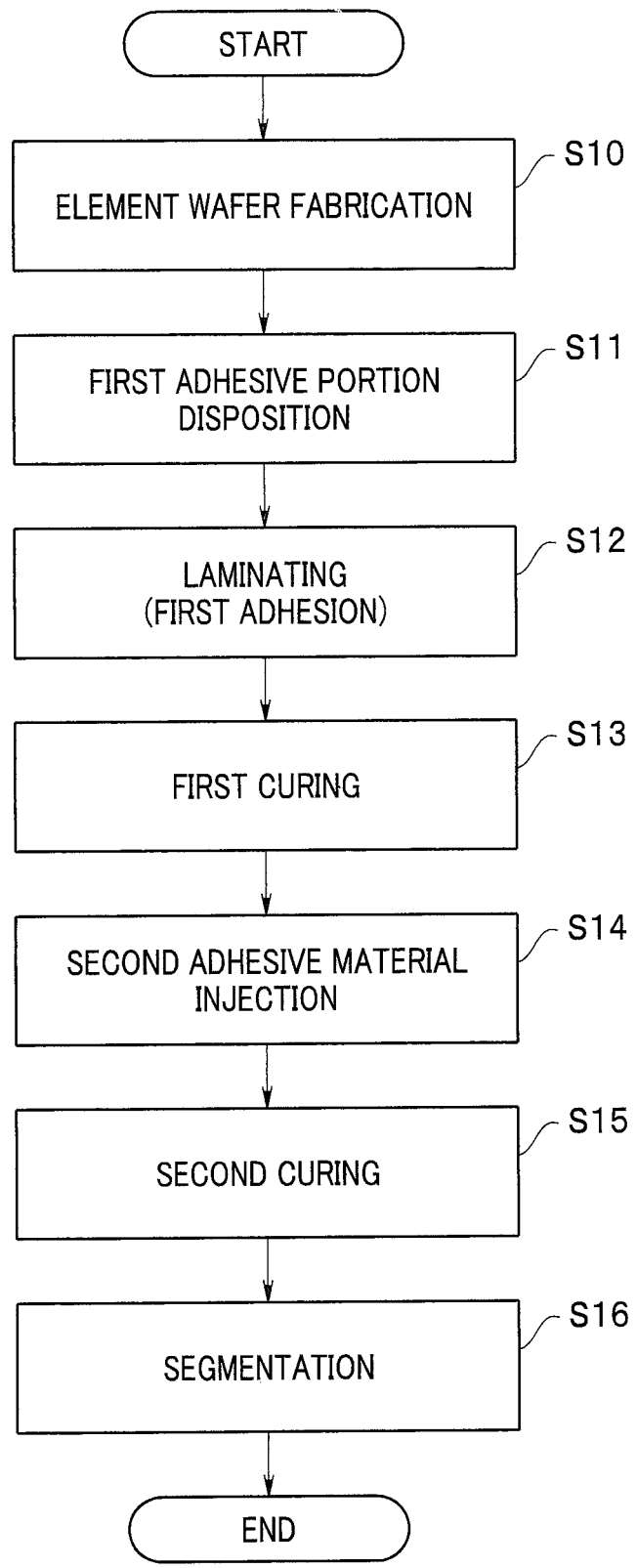
FIG. 5 is a flowchart of a manufacturing method of the optical unit according to the first embodiment.

Next, the manufacturing method of the optical unit for endoscope according to the present embodiment will be described referring to the flowchart in FIG. 5. As already described above, the optical unit 1 is a wafer-level optical unit manufactured by cutting and segmenting the bonded wafer 1W (see FIG. 11). Note that the description below includes a description on a region on each of the wafers corresponding to one optical unit. (That is, in some parts, only one of the plurality of components on each of the wafers will be described for simplifying the description).

<Step S10> Element Wafer Fabrication Process

Figure 6:
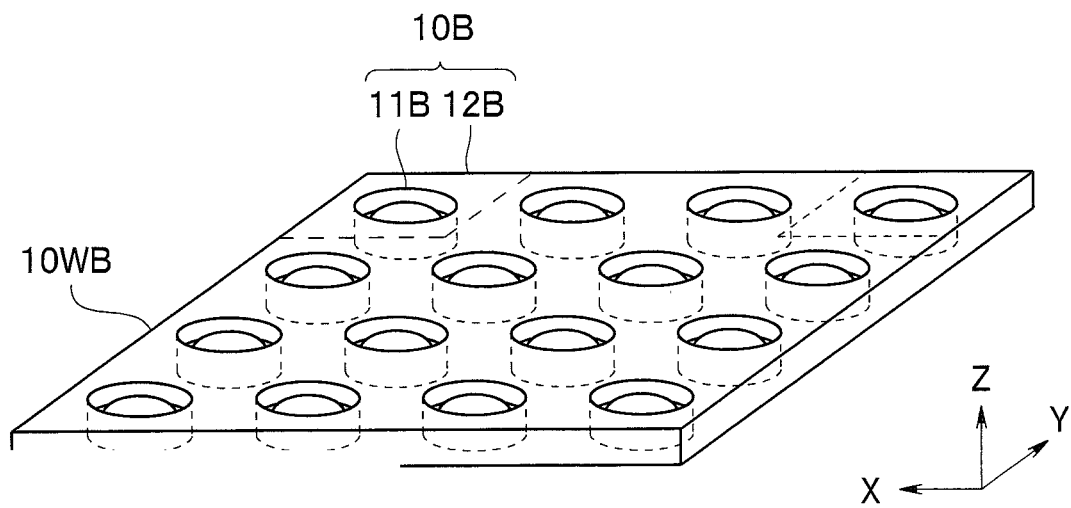
FIG. 6 is a perspective view of an element wafer of the optical unit according to the first embodiment.

The plurality of element wafers 10WA to 10WD respectively including at least one of the optical elements 10A to 10D are fabricated based on the specifications. For example, as shown in FIG. 6, the element wafer 10WB is a square wafer on which sixteen optical elements 10B, each of which includes the optical path portion 11B and the spacer portion 12B surrounding the optical path portion 11B, are arranged in a matrix form. The boundary lines between the respective adjacent optical elements 10B are cutting lines CL (see FIG. 13) to be used in the cutting process to be described later. That is, in the state of the element wafer 10W, the spacer portions 12B are a parallel flat plate region that surrounds the optical path portions 11B.

The element wafer 10WB is made of a transparent optical resin such as polycarbonate. The element wafer 10WB, which includes a plurality of optical path portions 11B formed in a predetermined shape, is fabricated by molding the optical resin using a metal mold by an injection molding method or by a press molding method, for example. The shape of the metal mold is transferred to the shape of the element wafer 10WB, which enables aspherical lenses to be easily fabricated as the optical path portions 11.

The element wafer 10WB has only to be transparent in the wavelength band of the light in the specifications of the optical unit, and may be fabricated by performing etching treatment on a glass such as a borosilicate glass, a quartz glass, or a single-crystal sapphire, for example. Alternatively, the element wafer 10WB may be a hybrid lens wafer formed by disposing, on a parallel flat plate wafer, the optical path portions 11B and the spacer portions 12 that are made of resin.

The configuration of the element wafer 10W, that is, the material of the element wafer, the shape, number, arrangement, and outer shape of the optical elements 10 disposed on the element wafer are designed according to the specifications of the optical unit. However, it is preferable that the numbers and the arrangements of the optical elements 10A to 10C on the element wafers 10WA to 10WC are the same.

The parallel flat plate element wafer 10WD is a filter wafer made of an infrared ray cut material that removes the infrared ray (light of wavelength of 770 nm or over, for example). A plate glass wafer including, on a surface thereof, a band-pass filter that transmits only the light of a predetermined wavelength and cut the light of unnecessary wavelength may be used as the filter wafer.

<Step S11> First Adhesive Portion Disposition Process

The solid first adhesive portions 21 composed of the first adhesive patterned in a predetermined shape are disposed on the element wafer 10W.

Figure 7:
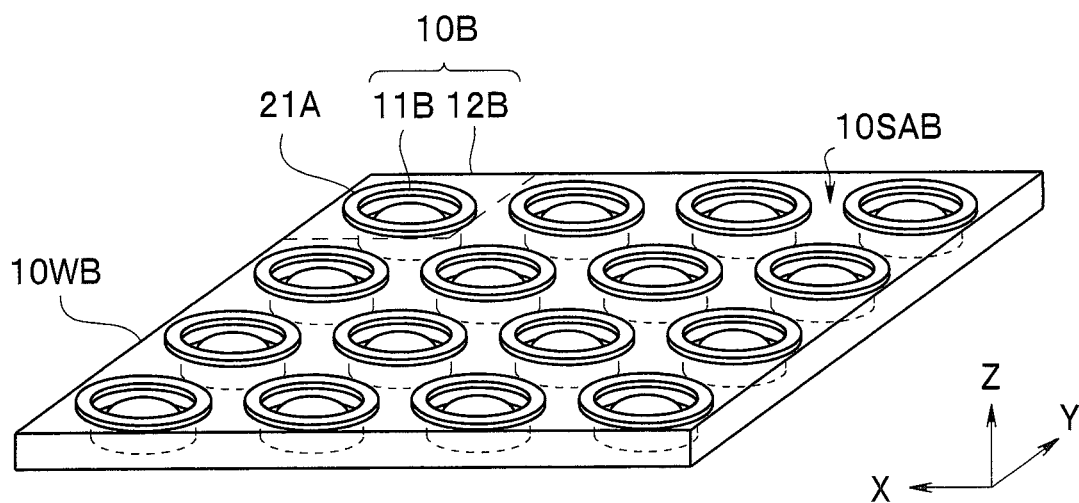
FIG. 7 is a perspective view of the element wafer of the optical unit according to the first embodiment.

For example, as shown in FIG. 7, the ring-shaped first adhesive portions 21A are disposed on the first principal surface 10SAB of the element wafer 10WB. The first adhesive portion 21 is disposed by applying the first adhesive, which is composed of photosensitive epoxy resin, photosensitive polyimide, or the like, to the entire surface of the first principal surface 10SAB, solidifying the first adhesive by drying with a hot plate at 120° C., and patterning the solidified first adhesive by the photolithography method. A film resist which is a photosensitive resin sheet may be used as the first adhesive.

With the patterning by the photolithography method, the film thickness, the disposing position, and the shape of the first adhesive portion 21 is defined with high precision. On the element wafer 10WB, the first adhesive portion 21 is patterned in a ring shape so as to surround the circular optical path portion 11B.

Figure 8:
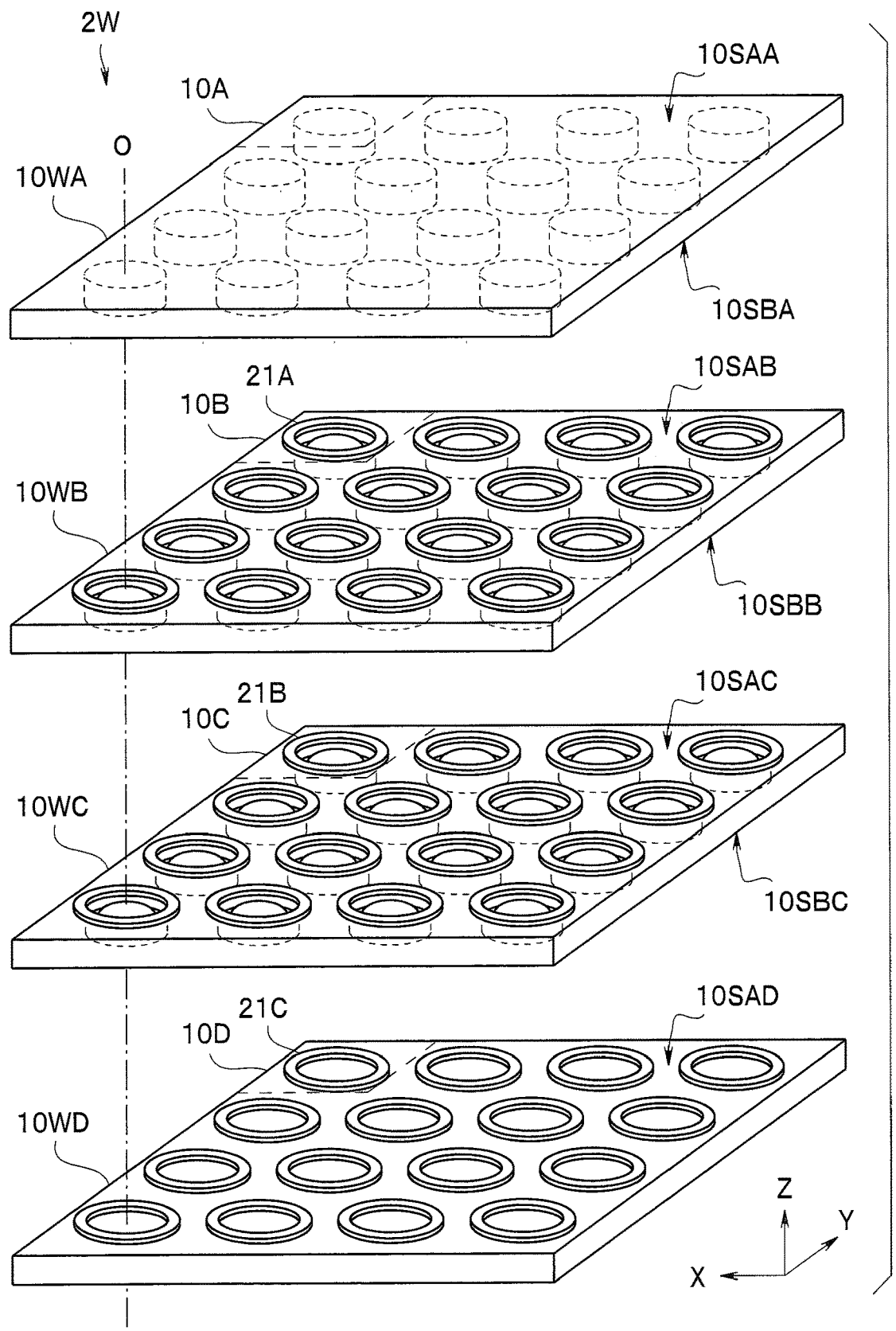
FIG. 8 is an exploded view of a laminated wafer of the optical unit according to the first embodiment.

As shown in FIG. 8, the first adhesive portions 21B, 21C are respectively disposed also on the first principal surface 10SAC of the element wafer 10WC and the first principal surface 10SAD of the element wafer 10WD.

Note that the first adhesive portions 21A for adhering the first element wafer 10WA and the second element wafer 10WB may be disposed on the second principal surface 10SBA of the first element wafer 10WA, or may be disposed on both of the second principal surface 10SBA of the first element wafer 10WA and the first principal surface 10SAB of the second element wafer 10WB, for example. Furthermore, the inner shape and the outer shape of the first adhesive portion 21 is a circular ring shape. However, at least one of the inner shape and the outer shape may be a polygonal shape or the like, as described later, as long as the first adhesive portion 21 surrounds the optical path space LS with no gap left.

The first adhesive portion 21 may be disposed by applying non-photosensitive first adhesive in a predetermined shape by a screen printing method, ink-jet method, or the like. However, in view of the precision of the film thickness, the disposing position, and the shape of the first adhesive portion 21, it is preferable to pattern the first adhesive portion by the photolithography method.

<Step S12> Laminating Process (First Adhesion Process)

Figure 9:
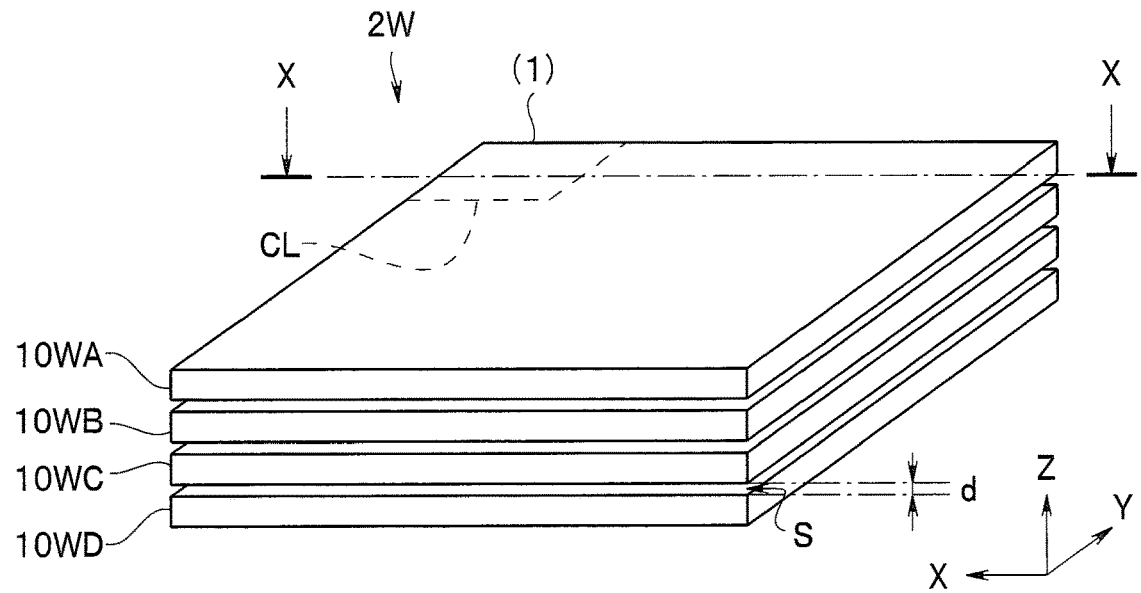
FIG. 9 is a perspective view of a laminated wafer of the optical unit according to the first embodiment.
Figure 10:
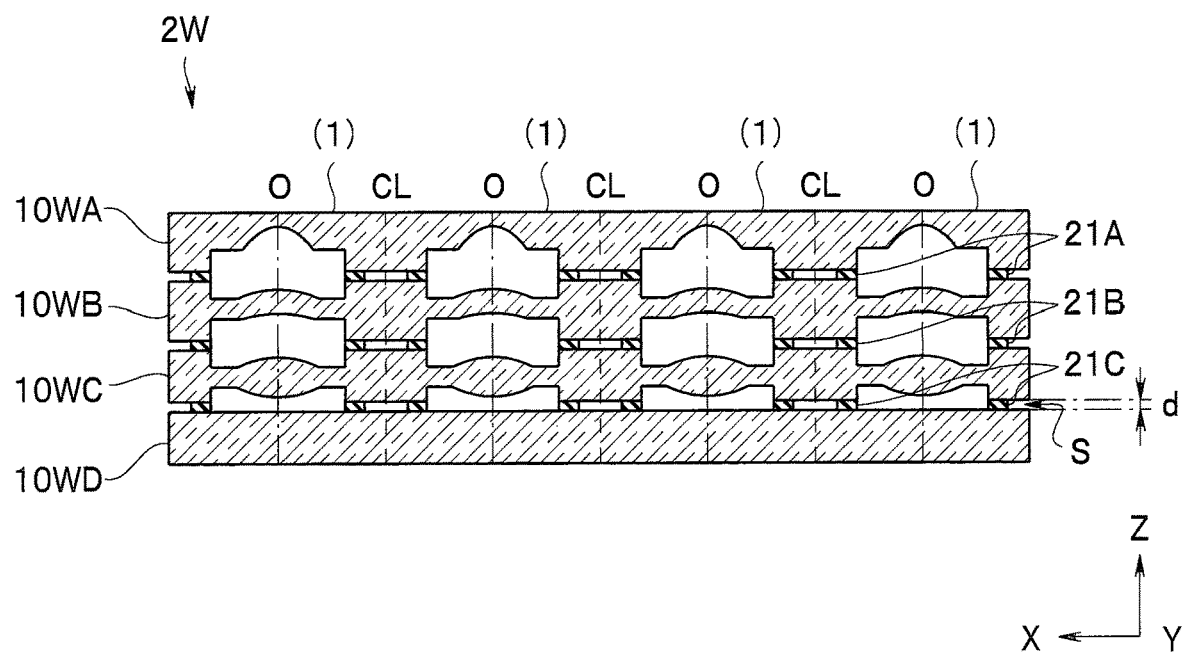
FIG. 10 is a cross-sectional view taken along the line X-X in FIG. 9 of the laminated wafer of the optical unit according to the first embodiment.

As shown in FIGS. 9 and 10, the plurality of element wafers 10WA to 10WD are arranged such that the optical axes O of the respective optical elements 10A to 10D coincide with each other, and thermally crimped, for example. The laminated wafer 2W is fabricated by the element wafers 10WA to 10WD being adhered to each other with the first adhesive portion 21 composed of the solid first adhesive disposed between the spacer portions 12 of the element wafers 10W opposed to each other. That is, when the uncured solid first adhesive (first adhesive portion 21) are crimped at 120° C., for example, the element wafers 10WA to 10WD are adhered to each other.

Note that it is preferable to perform the laminating process (first adhesion process) in a depressurized state below an atmospheric pressure, for example, equal to or lower than 0.1 barometric pressure. The pressure in the optical path space LS sealed by the first adhesive portion 21 is lower than the atmospheric pressure, which prevents the breakage of the laminated wafer due to an expansion of gas in the optical path space LS caused by heating in a subsequent process, for example, a reflow process. Note that the lower limit of the pressure is preferably set to 0.001 barometric pressure or more, for example, for simplification of the manufacturing processes.

<Step S13> First Curing Process

Curing treatment (first curing treatment) is performed on the first adhesive portion 21 of the laminated wafer 2W. In the manufacturing method according to the present embodiment, the first curing treatment is ultraviolet curing treatment.

The solid first adhesive portion 21 subjected to the curing treatment and having the thickness d, is patterned in the ring shape, which creates a gap having the thickness d between the opposed element wafers 10W of the laminated wafer 2W. That is, the first adhesive portion 21 has a pre-adhesion function and a function of a spacer that defines the thickness d of the gap between the optical elements 10.

Note that, if the first adhesive portion 21 is composed of a heat curable resin, the first curing treatment is a heating treatment. In addition, it is needless to say that curing process is not necessary in the case where the first adhesive portion 21 is not a curable resin but a thermoplastic resin.

<Step S14> Second Adhesive Injection Process

The first adhesive portion 21 is made of resin that is capable of being patterned, and the adhesive area is narrow. Therefore, the plurality of element wafers 10WA to 10WD are not strongly adhered to each other in the laminated wafer 2W. Therefore, liquid second adhesives 22A to 22C are injected from the side surfaces of the laminated wafer 2W into the space having the thickness (distance) d between the plurality of element wafers 10W with no gap left, and thereby the bonded wafer 1W is fabricated.

The second adhesives 22A to 22C are curable resins such as epoxy resin, acrylic resin, silicone resin, or the like. The adhesive strength of the second adhesive 22 is higher than the adhesive strength of the first adhesive 21, and the space around the first adhesive portion 21 is filled with the second adhesive with no gap left.

The second adhesive is liquid. However, the optical path space LS is surrounded by the ring-shaped first adhesive portion 21, which prevents the second adhesive 22 from entering the optical path space.

It is preferable to take advantage of capillary action in order to dispose the second adhesive 22 between the element wafers 10W of the bonded wafer 1W with no gap left. Therefore, it is preferable that the thickness d of the gap (distance between the opposed element wafers) is not less than 1 μm and not more than 50 μm.

In addition, in order to fill the gap between the element wafers 10W with the second adhesive 22A to 22C with no gap left, also the second adhesive injection process (second adhesion process) is preferably performed in a depressurized state below the atmospheric pressure, for example, equal to or lower than 0.1 barometric pressure, so that air does not remain in the gap, similarly as in the first adhesion process.

<Step S15> (Second) Curing Process

The liquid second adhesives 22A to 22C injected in the respective gaps between the element wafers 10WA to 10WD in the laminated wafer 2W are solidified by the curing treatment (second curing).

That is, if the second adhesive 22 is an ultraviolet curable resin, the second adhesive 22 is irradiated with ultraviolet, and if the second adhesive 22 is a heat curable resin, the second adhesive 22 is subjected to heating treatment. With the second curing, the liquid second adhesive 22 is solidified, and thereby the element wafers 10W are adhered to each other with strong adhesion force.

Note that if the first adhesive 21 and the second adhesive 22 are heat curable resins, the curing reaction of the first adhesive 21 further proceeds in the second curing process. Therefore, the curing temperature T1 of the first adhesive 21 in the first curing process is set to be higher than the curing temperature T2 of the second adhesive 22 in the second curing process. For example, when the curing temperature T1 in the first curing process is 180° C., the curing temperature T2 in the second curing process is set to be 100° C. to 150° C.

In addition, it is needless to say that the curing temperature T2 in the second curing process is set to be lower than the heat resistant temperature (softening temperature) of the first adhesive 21, if the first adhesive 21 is an ultraviolet curable resin or a thermoplastic resin.

<Step S16> Cutting Process

Figure 13:
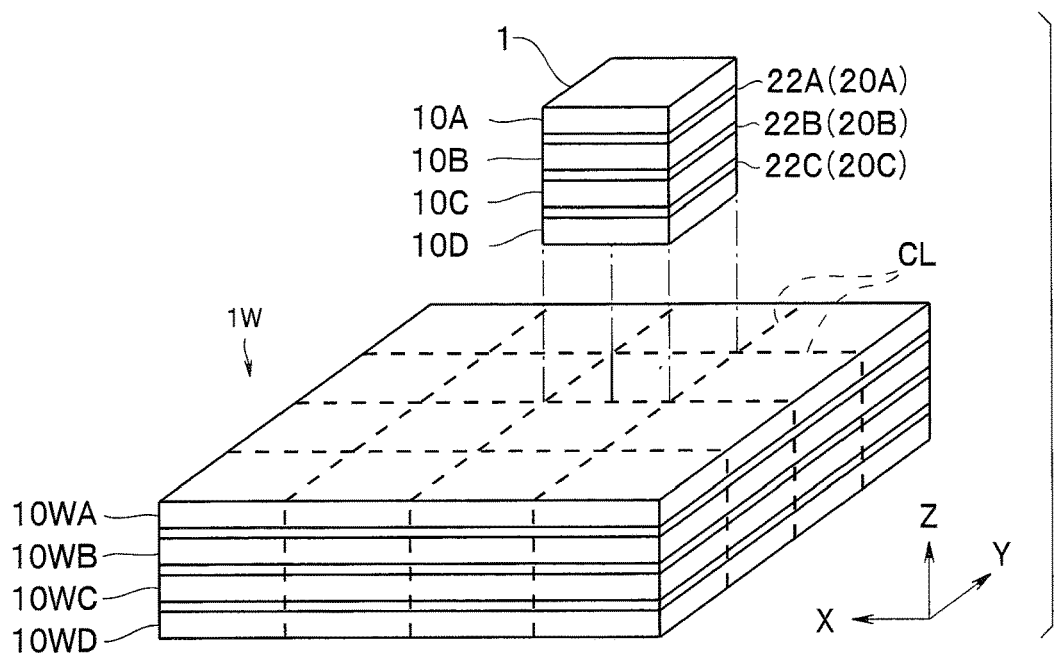
FIG. 13 is a perspective view of a cutting process of the bonded wafer of the optical unit according to the first embodiment.

As shown in FIG. 13, the bonded wafer 1W is cut along the cutting lines CL by a dicing blade and segmented into a plurality of optical units 1. The cutting may be performed by laser dicing or plasma dicing.

Note that the optical unit 1 has a rectangular parallelepiped shape. However, the bonded wafer 1W may be segmented into polygonal optical units having a hexagonal shape, for example, by the arrangement of the cutting lines CL of the bonded wafer 1W. In addition, the optical unit may be formed in a columnar shape by the processing after the segmentation. That is, the shape of the optical unit is not limited to the rectangular parallelepiped shape.

The gap around the first adhesive portion 21 is filled with the second adhesive portion 22 with no gap left, which allows the second adhesive portion 22 to expose on the four side surfaces of the optical unit 1.

As described above, the manufacturing method according to the present embodiment includes: the process S10 of fabricating the element wafers 10WA to 10WD; the process S11 of disposing the solid first adhesive portion 21 on the element wafer 10W; the first adhesion process S12 of fabricating the laminated wafer 2W; the first curing process S13 of performing the curing treatment on the first adhesive portion 21; the second adhesion process S14 of fabricating the bonded wafer 1W by injecting the liquid second adhesive; the second curing process S15 of performing the curing treatment on the second adhesive to form the second adhesive portion 22; and the process of cutting the bonded wafer 1W.

The plurality of element wafers 10WA to 10WD respectively include the optical elements 10A to 10D, and the optical elements respectively include the plurality of optical path portions 11 and the spacer portions 12 surrounding the respective optical path portions 11. The first adhesive portion 21 is composed of the first adhesive which is a photosensitive resin, and patterned by the photolithography method in a ring shape so as to surround the periphery of the optical path space with no gap left. The liquid second adhesive is injected into the gap created by the thickness d of the first adhesive portion 21, so as to surround the periphery of the first adhesive portion 21 with no gap left by the capillary action.

According to the manufacturing method of the present embodiment, the liquid adhesive is not likely to protrude to the optical path space, which results in easy manufacturing. In addition, the distance d between the optical elements 10 is defined by the first adhesive portion 21 and the optical elements 10 are strongly adhered to each other with the second adhesive portion 22, which results in high reliability.

Modified Examples of First Embodiment

Next, optical units 1A to 1E according to the modified examples of the first embodiment will be described. The optical units 1A to 1E are similar to the optical unit 1 and have the same effects as those of the optical unit 1. The same constituent elements are attached with the same reference numerals and descriptions thereof will be omitted.

Modified Example 1 of the First Embodiment

Figure 14:
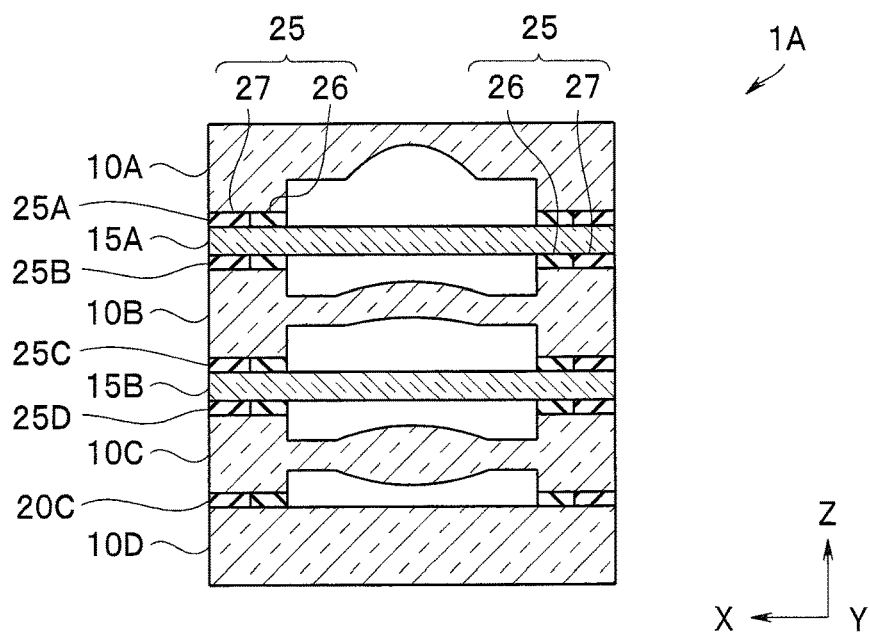
FIG. 14 is a cross-sectional view of an optical unit according to a modified example 1 of the first embodiment.

As shown in FIG. 14, in the optical unit 1A according to the present modified example, among the plurality of laminated optical elements 10A to 10D and optical elements 15A and 15B, the optical elements 15A and 15B are middle elements made of transparent parallel flat plates.

The optical element 15 is a spacer element that defines the distance between the optical elements 10, and is also an adhesive element for easily adhering the element wafers 10 to each other. That is, in order to perform patterning on the first adhesive portion 21 by the photolithography method, for example, the photo resist, which is the first adhesive, is required to be applied to the first principal surface 10SAB of the element wafer 10WB with even thickness. However, the first principal surface 10SAB includes the optical path portions 11B, which creates recessed portions. Therefore, there is a case where it is not easy to apply the first adhesive to the first principal surface 10SAB by a general application method such as a spin coater.

The optical element 15 of the optical unit 1A has a base body made of a parallel flat plate wafer with no recessed portion. Therefore, it is easy to apply the photo resist to the optical element 15. Thus, manufacturing of the optical unit 1A is easier than that of the optical unit 1.

Modified Example 2 of First Embodiment

Figure 15A:
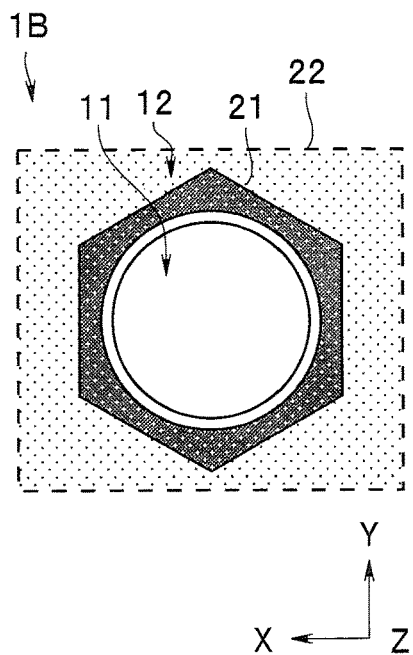
FIG. 15A is a top view of a bonding portion of an optical unit according to a modified example 2 of the first embodiment.

In the optical unit 1B according to the present modified example, the outer shape of the ring-shaped first adhesive portion 21 is hexagonal shape, as shown in FIG. 15A. On the other hand, the inner shape of the first adhesive portion 21 is circular shape, and the diameter (inner diameter) is larger than the outer diameter of the optical path portion 11 of the optical element 10, that is, the inner diameter of the spacer portion 12.

That is, the inner shape and the outer shape of the first adhesive portion 21 do not have to be a circular shape, as long as the first adhesive portion 21 surrounds the optical path space LS with no gap left. In other words, the "ring-shape" in the specification does not mean that the inner shape and the outer shape are limited to the circular ring shape. In addition, the inner dimension of the first adhesive portion 21 does not have to be equal to the inner dimension of the spacer portion 12 as long as there is no bad influence on the optical path space. Furthermore, all the plurality of first adhesive portions 21 of the optical units do not have to be formed in the same shape.

Modified Example 3 of First Embodiment

Figure 15B:
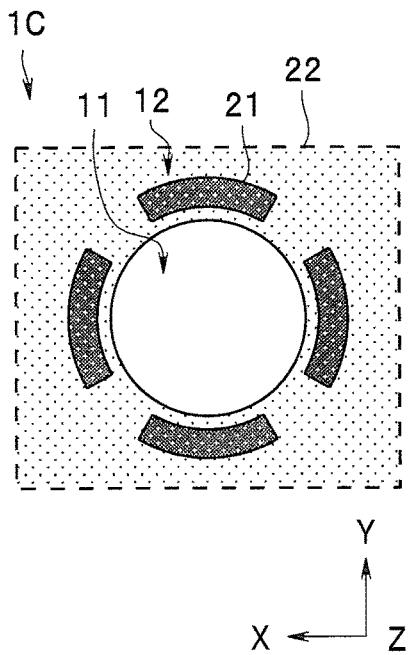
FIG. 15B is a top view of a bonding portion of an optical unit according to a modified example 3 of the first embodiment.

In the optical unit 1C according to the present modified example, four fan-shaped first adhesive portions 21 are arranged rotation-symmetrically, with the optical axis O as a center, as shown in FIG. 15B. Gaps exist between the respective four first adhesive portions 21, and the four first adhesive portions 21 surround the optical path portion 11 with gaps. That is, the first adhesive portion 21 is made of the solid first adhesive 21 disposed in a part of the gap between the spacer portions 12.

However, the second adhesive portion 22 disposed around the four first adhesive portions 21 has a ring shape that surrounds the optical path portion 11 of the optical element 10 with no gap left.

According to the manufacturing method of the optical unit 1C, the first adhesive portion 21 has a pre-adhesion function and a function of a spacer that defines the thickness d of the gap between the optical elements 10.

In the optical unit 1C, the liquid second adhesive is injected, by the capillary action, into the gap between the spacer portions 12 of the optical elements 10, the gap being created by the first adhesive portion 21. The height of the optical path space is sufficiently great (for example, more than 50 μm) with respect to the thickness (height) d of the gap. Therefore, there is no possibility that the second adhesive enters the optical path space by the capillary action.

Note that, in the manufacturing method of the optical unit 1C, it is preferable to perform the second adhesion process in a depressurized state below an atmospheric pressure. This enables the liquid second adhesive to be effectively injected into the gap between the optical elements 10, and also enables the optical path space LS to be sealed in the state below the atmospheric pressure.

Modified Examples 4, 5 of First Embodiment

Figure 15C:
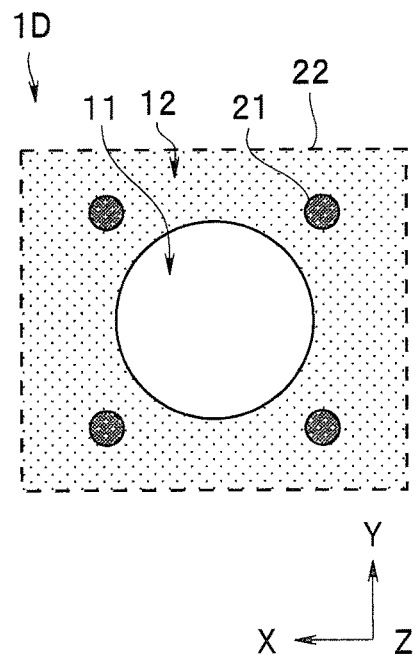
FIG. 15C is a top view of a bonding portion of an optical unit according to a modified example 4 of the first embodiment.
Figure 15D:
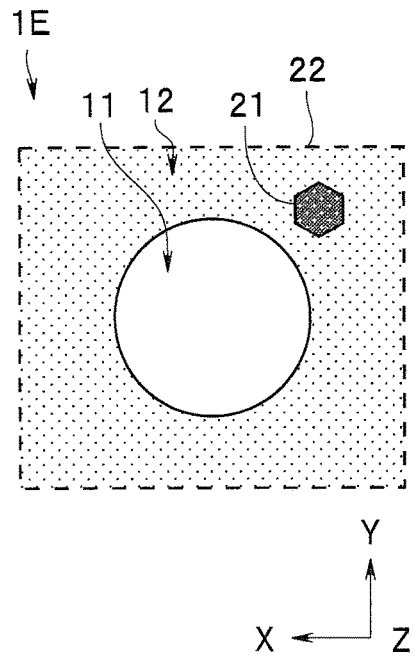
FIG. 15D is a top view of a bonding portion of an optical unit according to a modified example 5 of the first embodiment.

As shown in FIG. 15C, in the optical unit 1D according to the modified example 4, four circular first adhesive portions 21 are arranged rotation-symmetrically, with the optical path portion 11 as a center. As shown in FIG. 15D, in the optical unit 1E according to the modified example 5, one first adhesive portion 21 in a hexagonal shape is arranged.

In the optical units 1D, 1E, the optical path space is surrounded by the ring-shaped second adhesive portion 22 with no gap left. That is, if the first adhesive portion 21 has a pre-adhesion function and a function of a spacer that defines the thickness d of the gap between the optical elements 10 for fabricating the laminated wafer, the number and the shape of the first adhesive portion 21 can be appropriately selected.

Note that only one first adhesive portion 21 is disposed in the optical unit 1E. However, the element wafers are adhered to each other through the plurality of first adhesive portions 21. Therefore, at the time of fabrication of the laminated wafer, the plurality of element wafers are laminated such that the principal surfaces of the wafers are parallel with each other.

Note that if at least three first adhesive portions 21 are disposed on the respective element wafers, the plurality of element wafers are laminated with the principal surfaces being parallel with each other at the time of fabrication of the laminated wafer. In addition, the first adhesive portions 21 may be disposed on the element wafers so as to be located in regions which are not processed into the optical units. Therefore, the first adhesive portion 21 does not have to be disposed in all of the segmented optical units.

Second Embodiment

An optical unit 1F according to the second embodiment is similar to the optical units 1 to 1E and has the same effects as those of the optical units 1 to 1E. The same constituent elements are attached with the same reference numerals and descriptions thereof will be omitted.

Figure 16:
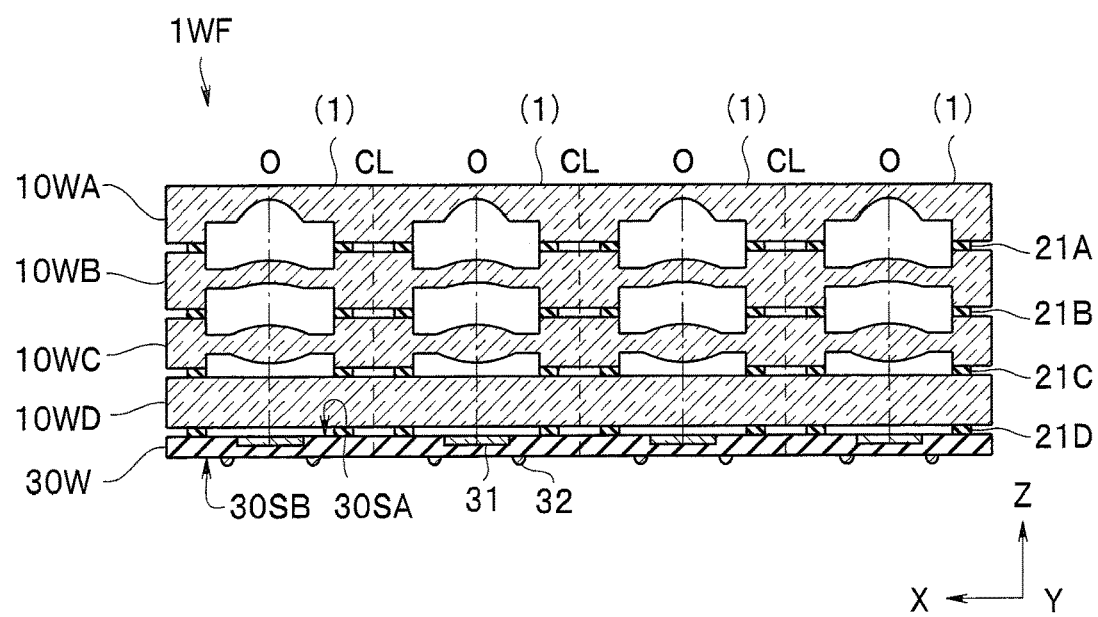
FIG. 16 is a cross-sectional view of a bonded wafer of an optical unit according to a second embodiment.

As shown in FIG. 16, in the first adhesion process of the optical unit 1F according to the second embodiment, a laminated wafer 2WF is fabricated, in which an image pickup device wafer 30W including image pickup devices 30 is adhered as an element wafer.

The image pickup device wafer 30W made of a silicon wafer includes a plurality of image pickup devices 30 each including, on a light-receiving surface 30SA, a light-receiving portion 31 and the like formed by a known semiconductor manufacturing technique. An electrode 32 connected to the light-receiving portion 31 through the through-wiring (not shown) is disposed on the rear surface 30SB of each of the image pickup devices 30. The image pickup device wafer 30W may include a reading circuit.

Figure 17:
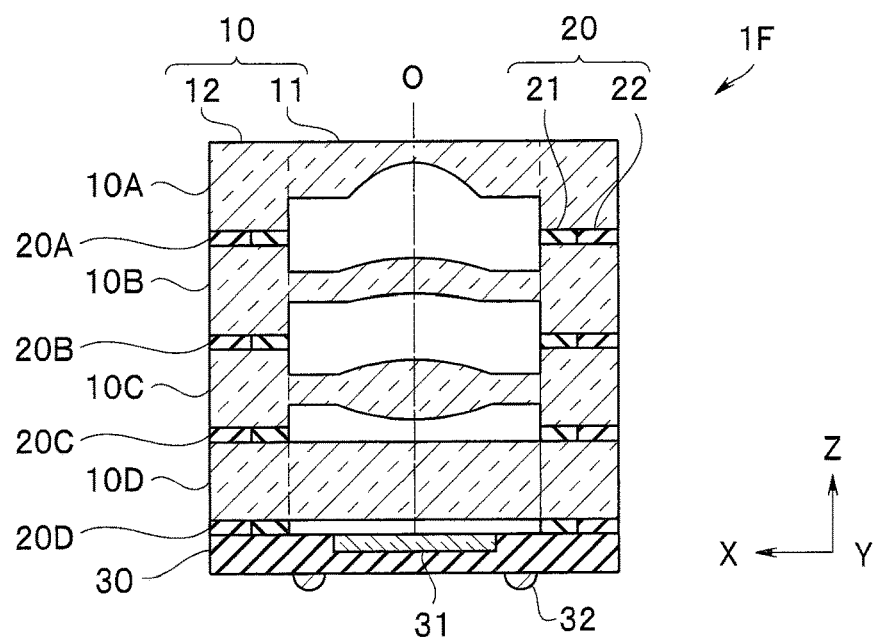
FIG. 17 is a cross-sectional view of the optical unit according to the second embodiment.

As shown in FIG. 17, the optical unit 1F fabricated by cutting the laminated wafer 2WF is an image pickup unit including the image pickup device 30.

The light received by the light-receiving portion 31 of the image pickup device 30 through the optical elements 10A to 10D is converted into an electric signal and outputted from the electrode 32.

Note that it is needless to say that the optical unit 1F according to the second embodiment includes the effects of the respective optical units 1A to 1E, if the optical unit 1F includes the configurations of the optical unit 1A to 1E according to the modified examples of the first embodiment. Furthermore, it is needless to say that the endoscopes including the optical units 1A to 1F have the same effects as those of the endoscope 9 including the optical unit 1, and further include the respective effects of the respective optical units 1A to 1F.

The present invention is not limited to the above-described embodiments, etc., but various changes, modifications, and the like are possible without changing the gist of the present invention.

What is claimed is:

1. A method for manufacturing an optical unit, the method comprising:
    fabricating a plurality of element wafers each of the plurality of element wafers including a plurality of optical elements, each optical element of the plurality of optical elements including an optical path area and a spacer area surrounding the optical path area;
    arranging the plurality of element wafers such that optical axes of the plurality of optical elements on one of the plurality of element wafers coincide with corresponding optical elements on each other of the plurality of element wafers when the element wafers are stacked on each other;
    adhering opposing element wafers of the plurality of element wafers to each other with a first adhesive made of a solid resin disposed between a first portion of the spacer area of each of the plurality of optical elements of the opposing element wafers to fabricate a laminated wafer in which a distance between the spacer area of each of the plurality of optical elements of the opposing element wafers is defined by the first adhesive to prevent contact between the opposing element wafers, the first adhesive creating a gap between a second portion of the spacer area of each of the plurality of optical elements of the opposing element wafers;
    injecting a second adhesive in a liquid resin form in the gap;
    performing curing treatment on the second adhesive, to cause the second adhesive in the liquid resin to become a solid second adhesive to form a bonded wafer; and
    cutting the bonded wafer after the curing treatment to separate the bonded wafer into the optical unit.

2. The method according to claim 1, wherein the second adhesive is injected into the gap by a capillary action.

3. The method according to claim 2, wherein the first adhesive is made of a photosensitive resin patterned on the first portion of the spacer area of each of the plurality of optical elements of the opposing element wafers by a photolithography method.

4. The method according to claim 1, wherein
    the first portion of the spacer area is a ring shape so as to surround a periphery of the optical path area to completely enclose the optical path area, and
    the second portion of the spacer area surrounds a periphery of the first portion to completely fill the gap.

5. The method according to claim 1, wherein
    the first adhesive and the second adhesive are heat curable resins, and
    a curing temperature of the first adhesive is higher than a curing temperature of the second adhesive.

6. The method according to claim 1, wherein the adhering and the injecting are performed in a depressurized state below an atmospheric pressure.

7. The method according to claim 1, further comprising disposing a transparent parallel flat plate disposed between adjacent element wafers of the plurality of element wafers.

8. The method according to claim 1, further comprising, prior to the cutting, adhering an image pickup device wafer having a plurality of image pickup devices to the bonded wafer.

9. An optical unit for endoscope, the optical unit comprising:
- a plurality of optical elements each including an optical path area and a spacer area surrounding the optical path area, the plurality of optical elements being laminated; and
- an adhesive for adhering opposed optical elements of the plurality of optical elements to each other, the adhesive being disposed between spacer areas of the opposed optical elements,
- wherein the adhesive includes a first adhesive which is a solid resin and a second adhesive which is a liquid resin, a distance between the spacer areas of the opposed optical elements is defined by the first adhesive to prevent contact between the opposed optical elements, the first adhesive creating a gap between the spacer areas of the opposed optical elements and the second adhesive is disposed in the gap.

10. The optical unit for endoscope according to claim 9, wherein
- the first adhesive has a ring shape that surrounds the optical path area, and
- the second adhesive surrounds a periphery of the first adhesive portion to completely fill the gap.

11. The optical unit for endoscope according to claim 9, wherein a pressure in the optical path area is lower than an atmospheric pressure.

12. The optical unit for endoscope according to claim 9, further comprising a transparent parallel flat plate disposed between adjacent optical elements of the plurality of optical elements.

13. An optical unit for an endoscope, the optical unit comprising:
- a plurality of optical elements each including an optical path area and a spacer area surrounding the optical path area, the plurality of optical elements being laminated;
- an adhesive for adhering opposed optical elements of the plurality of optical elements to each other, the adhesive being disposed between spacer areas of the opposed optical elements; and
- an image pickup device disposed on one of the plurality of optical elements;
- wherein the adhesive includes a first adhesive which is a solid resin and a second adhesive which is a liquid resin, a distance between the spacer areas of the opposed optical elements is defined by the first adhesive to prevent contact between the opposed optical elements, the first adhesive creating a gap between the spacer areas of the opposed optical elements and the second adhesive is disposed in the gap.

14. An endoscope comprising:
an optical unit comprising:
- a plurality of optical elements each including an optical path area and a spacer area surrounding the optical path area, the plurality of optical elements being laminated; and
- an adhesive for adhering opposed optical elements of the plurality of optical elements to each other, the adhesive being disposed between spacer areas of the opposed optical elements,
- wherein the adhesive includes a first adhesive which is a solid resin and a second adhesive which is a liquid resin, a distance between the spacer areas of the opposed optical elements is defined by the first adhesive to prevent contact between the opposed optical elements, the first adhesive creating a gap between the spacer areas of the opposed optical elements and the second adhesive is disposed in the gap.

* * * * *

UNITED STATES PATENT AND TRADEMARK OFFICE
CERTIFICATE OF CORRECTION

PATENT NO. : 10,624,527 B2
APPLICATION NO. : 16/204575
DATED : April 21, 2020
INVENTOR(S) : Kazuya Maeda It is certified that error appears in the above-identified patent and that said Letters Patent is hereby corrected as shown below:

In the Claims

Column 12, Claim 1, Line 12 should read:
fabricating a plurality of element wafers, each of the Signed and Sealed this
Thirteenth Day of October, 2020

Andrei Iancu
*Director of the United States Patent and Trademark Office*